United States Patent [19]
Glassel et al.

[11] Patent Number: 5,692,907
[45] Date of Patent: Dec. 2, 1997

[54] INTERACTIVE CARDIAC RHYTHM SIMULATOR

[75] Inventors: Philip R. Glassel, Stacy; Michael D. Miller, Minneapolis, both of Minn.

[73] Assignee: Pacesetter, Inc., Sylmar, Calif.

[21] Appl. No.: 515,553

[22] Filed: Aug. 16, 1995

[51] Int. Cl.$^6$ .................................................. G09B 23/28
[52] U.S. Cl. ........................ 434/262; 434/267; 434/272
[58] Field of Search ............................... 434/262, 267, 434/268, 272

[56] References Cited

U.S. PATENT DOCUMENTS 4,639,223  1/1987  Keller, Jr. ............................. 434/272

OTHER PUBLICATIONS

Steinhaus B.M.; Wells R. T.; Hursta W.N.; A PC-based Real-time Simulator of Cardiac Bradycardia and Tachycardia Arrhythmias; Proceedings of Computer in Cardiology 1992 pp. 587-590, Oct. 1992.

*Primary Examiner*—Richard J. Apley
*Assistant Examiner*—John Rovnak

[57] ABSTRACT

A system for simulating the activity of the heart includes a computer controlled heart model for generating and displaying simulated electrogram signals. To accomplish this task, the simulation system includes various hardware components and software designed to realize a heart model and generate electrogram display data. Based on the recognition that groups of cells (tissue groups) of the heart can be selected such that the electrical characteristics of the tissue group, as a whole, resembles the simple electronic characteristics of an individual cell, the model is designed to simulate the electrical activities and interaction of multiple tissue groups. With this approach, each tissue group is associated with a software controlled state machine that changes states in response to stimulation signals from other tissue groups, internal or external sources, or timer expirations.

20 Claims, 11 Drawing Sheets

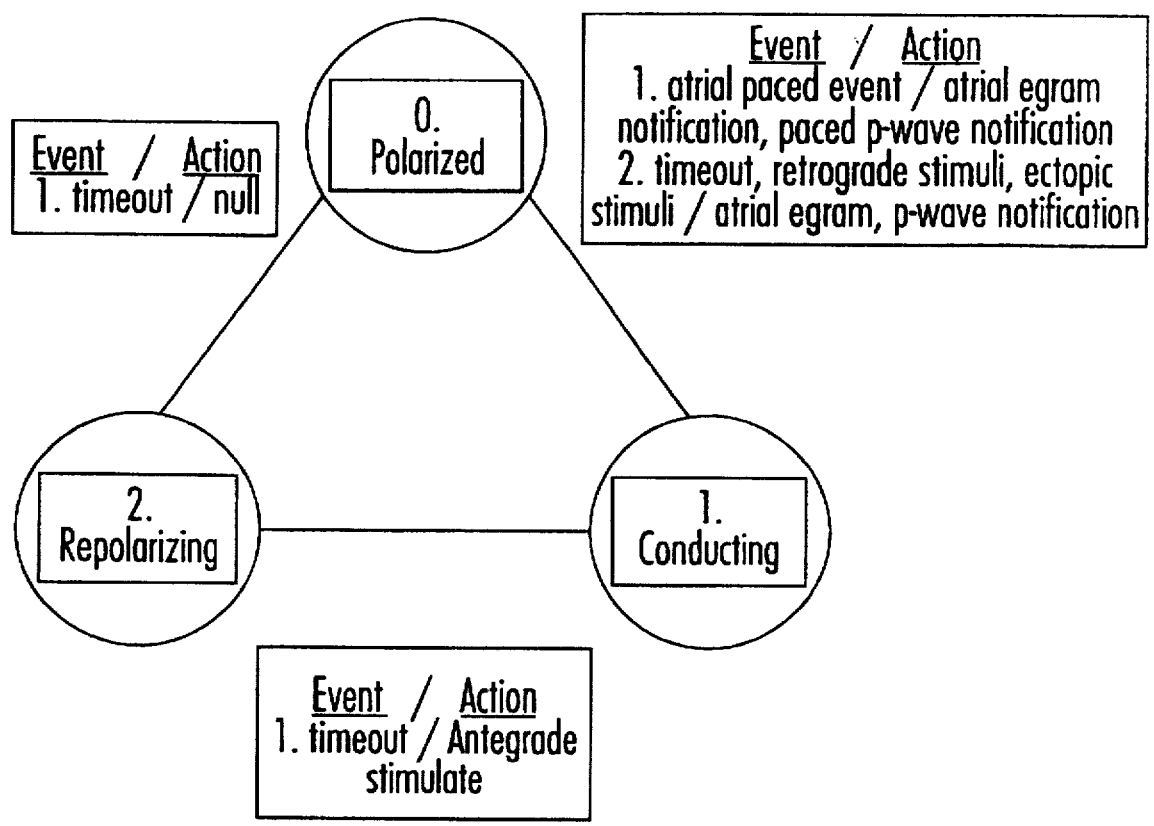
FIG. 6(a) SA NODE MODEL
STATE TRANSITION DIAGRAM

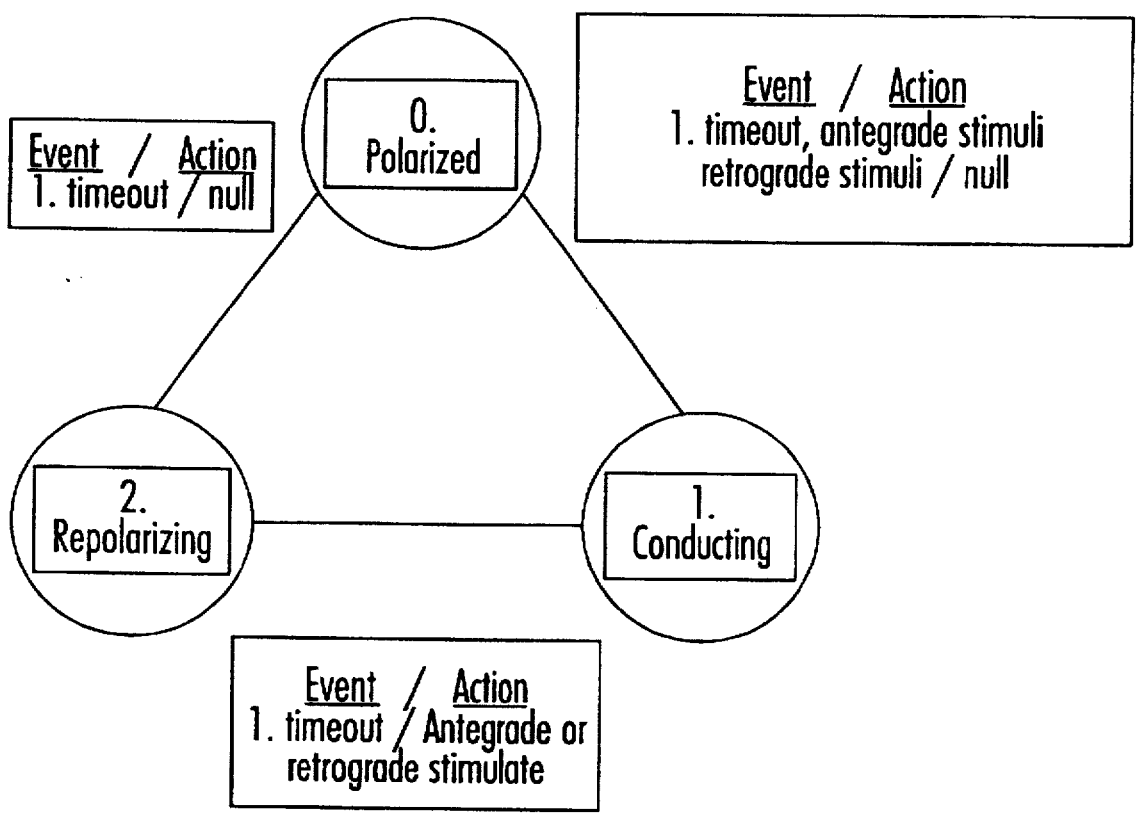
FIG. 6(b) MIT MODEL
STATE TRANSITION DIAGRAM

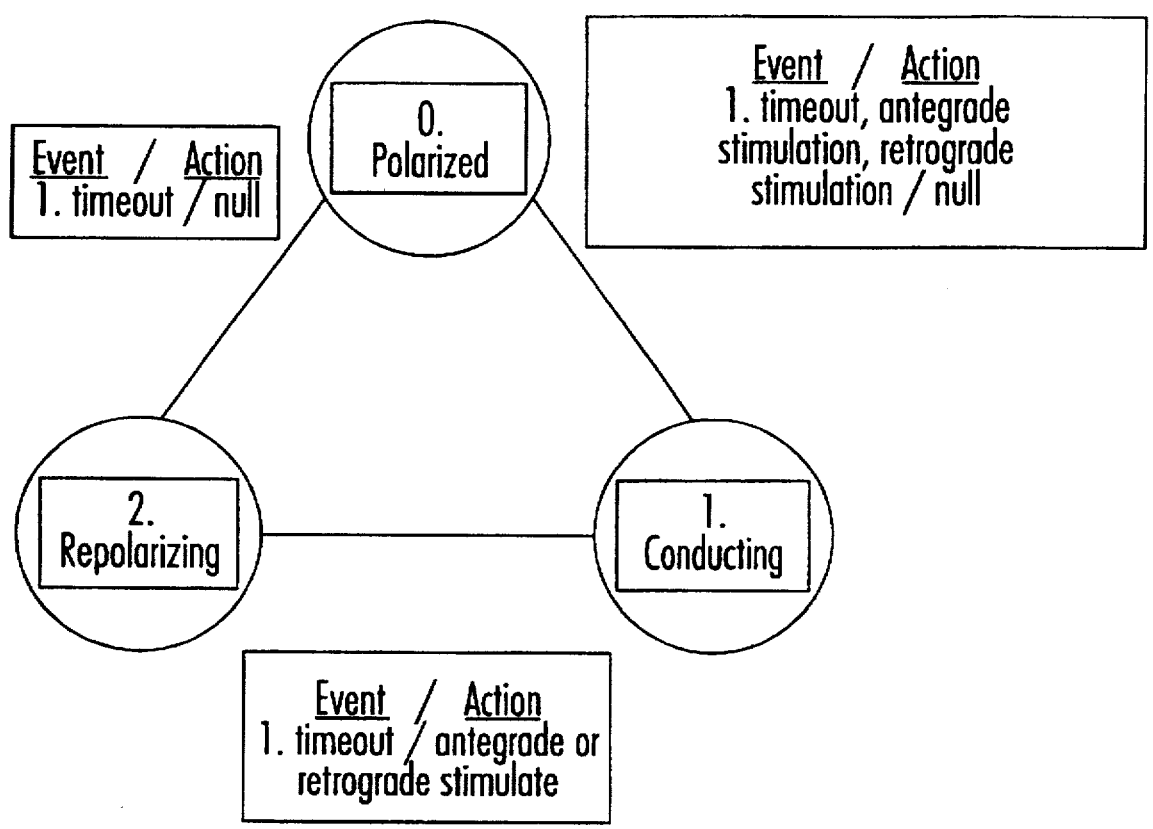
FIG. 6(c) AV NODE MODEL STATE TRANSITION DIAGRAM

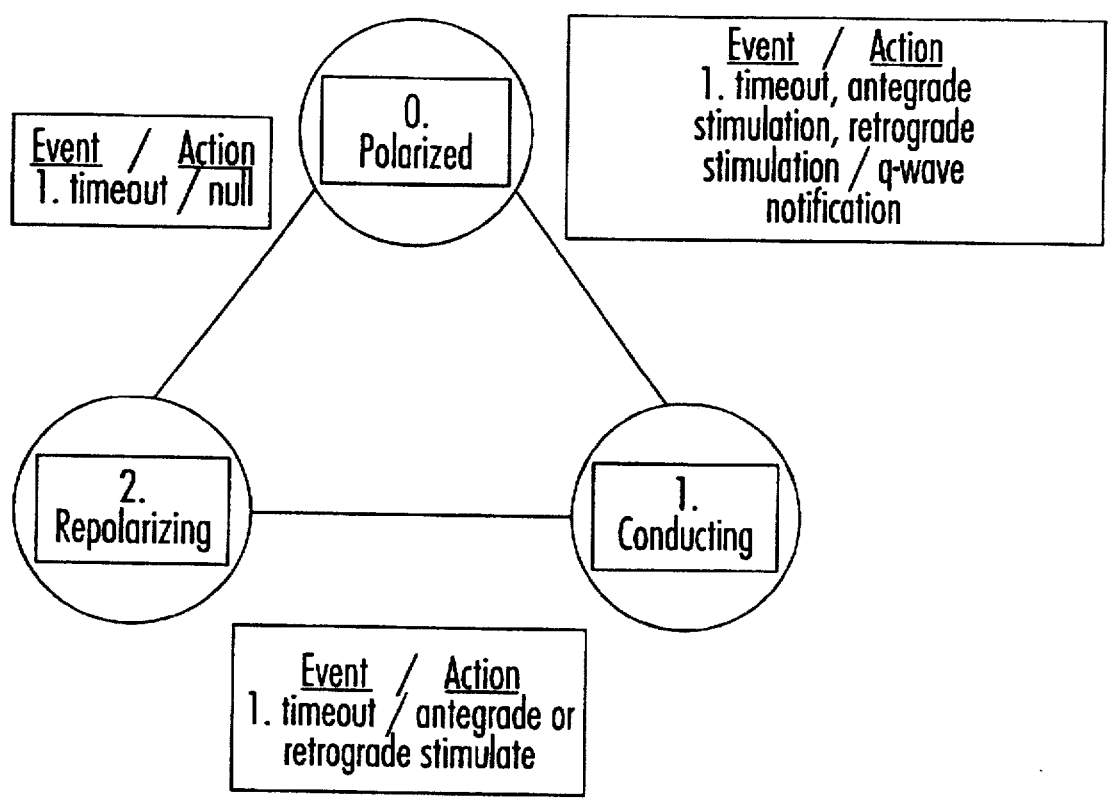
FIG. 6(d) HIS MODEL
STATE TRANSITION DIAGRAM

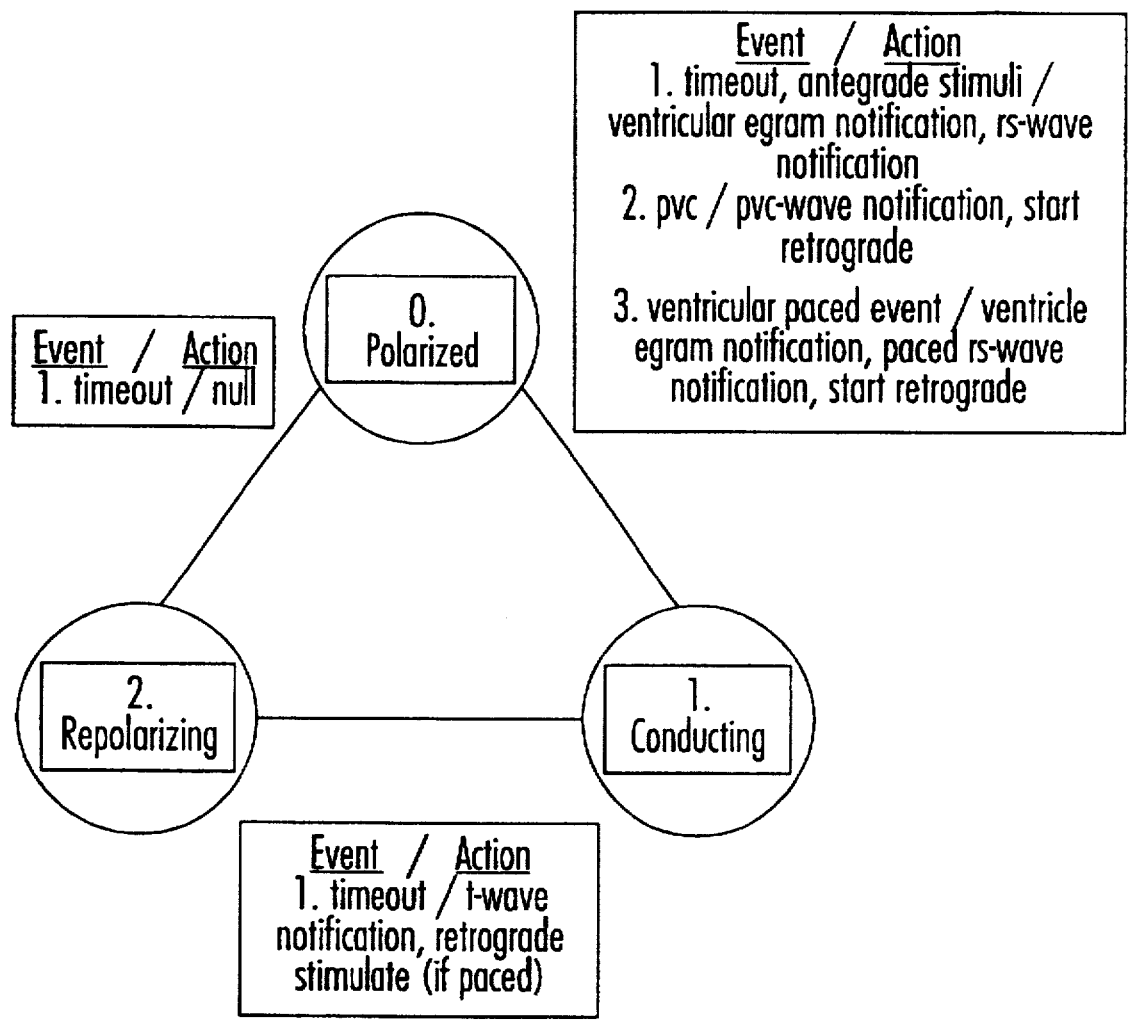
FIG. 6(e) VENTRICLE MODEL
STATE TRANSITION DIAGRAM

INTERACTIVE CARDIAC RHYTHM SIMULATOR

FIELD OF THE INVENTION

The present invention relates to apparatus and methods for simulating the activity of the heart and, in preferred embodiments, for simulating and testing effects of medical treatments on the heart.

BACKGROUND OF THE INVENTION

Before describing the present invention in detail, it will be instructive to briefly review some fundamental principles associated with the heart and electrogram signals. FIG. 1 shows a simplified drawing of a heart. For purposes of clarity, many elements of the heart have been omitted from the drawing of FIG. 1.

The heart shown in FIG. 1 includes four chambers: a right atrium 10, a right ventricle 12, a left atrium 14, and a left ventricle 16. The atriums function as reservoirs and the ventricles function as pumps for pumping blood through the body. Blood, carrying carbon dioxide from the body, enters the right atrium chamber 10 through the superior vena cava 18 and the inferior vena cava 20. The right ventricle pumps blood into the pulmonary artery 22, to the right and left lungs. Oxygenated blood from the lungs enters the left atrium chamber through the pulmonary vein 24 and is thereafter pumped into the aorta 26 by the left ventricle 16. The rhythmatic movement of the heart involves a contraction of the atrium chambers, to deliver blood to the ventricle chambers, followed by a contraction of the ventricle chambers, to pump blood through the pulmonary artery 22 and the aorta 26. These contractions are controlled by a complex interaction of electrical impulses and electrical characteristics of the heart tissue.

In general, the electrical impulse 28 in a normal waveform begins at the S-A node 30 in the atrium chamber 10. Other nodes in the heart may function as an impulse source, for example, upon disfunction of the S-A node or other abnormal cardiac function. The electrical impulse 28 causes depolarization of the muscle tissue in the atrium chambers, resulting in an atrial contraction. The electrical impulse 28 propagates to the His node 32 and through the A-V bundle 34 and the right and left branches 36 and 38. The right and left bundle branches 36 and 38 distribute the electrical impulse through the heart muscle, resulting in a contraction of the ventricles.

The electrical impulses of a heart generate electrical waveforms which can be sensed by electrodes placed on the chest, for example, with a surface electrogram (ECG) system. A typical waveform generated by a heart (as shown in FIG. 2) includes a P-wave associated with the depolarization of the atria, a QRS-wave (also called a QRS complex) associated with the propagation of the electrical impulse from the A-V node, through the right and left bundle branches for depolarization of the ventricals, and the T-wave associated with the repolarization of the ventricles. The repolarization of the atria is typically not sensed, as it typically occurs during the QRS-wave. One typical cardiac waveform cycle, therefore, includes a P-wave, a QRS complex, and a T-wave. The electrical waveforms generated by a heart can be sensed and displayed as an electrogram, to study the operation of the heart. Various cardiac pathologies result in distortions in the cardiac waveform and can, therefore, be studied by viewing the cardiac waveform.

For many patients with cardiac pathologies, cardiac pacemakers have been used to provide stimulation pulses to the heart tissue to control the cardiac waveform, for example, to control the rate at which the heart chambers contract. Modern cardiac pacemakers include the dual chamber type (adapted to provide atrial stimulation pulses, or "A-pulses", and ventricle stimulation pulses, or "V-pulses") and single chamber pacemakers (for example, for providing ventricle stimulation pulses). Stimulation pulses from a cardiac pacemaker can also be sensed and displayed with the cardiac waveform.

A cardiac waveform may be electronically simulated for a variety of purposes, such as medical testing, medical demonstrations or educational demonstrations. There are a number of approaches that can be taken to simulate the activity of the heart. In the past it was sufficient to simply quantify and juxtapose various surface ECG waveforms based on a relatively few basic arrhythmia patterns. According to typical earlier approaches to simulating heart activity, signals representing classical P-wave and a few classical QRS-complexes were stored and displayed using relatively simple timing sequences and algorithms.

This approach has been successful in demonstrating and testing simple, traditional Brady pacemaking techniques. However, as the pacing industry becomes more sophisticated, this approach has rapidly become more and more unmanageable due to the sheer number of combinations of waveforms and the complexity or their interactions with each other. These interactions become very difficult to quantify, specify, and predict with ordinary logic, particularly when the interaction of a real, or simulated pacemaker is introduced into the simulation. Accordingly, there is a need for a more accurate and versatile system and method for simulating the activity of the heart.

The electrical activity of the heart is affected by the electrical characteristics, events and interactions of individual cells of the heart. If unlimited computational power were available, an interesting approach would be to simulate the electrical characteristics and activity of every cell in the heart. This approach would have the advantage that the generated ECG waveforms would be a function of the current state of electrical activity for all of the cells in the simulation, weighted by a function that accounts for the non-cardiac tissue that must be traversed to reach the surface ECG lead. Furthermore, an endocardial electrogram could be derived for any particular point of interest within the heart.

If such a model could be set up correctly, any heart anomaly and pacing therapy could be simulated and the results of that therapy could be predicted. The correctness of the algorithm would not be dependent upon the programmer's intimate knowledge of ECG strip charts and their interpretation, but rather it would be based on simple building blocks using electrical conduction principles.

Since each cell has relatively simple characteristics, a model based on this concept would be relatively easy to implement. However, the number of cells being simulated would be massive. Accordingly, a model involving a simulation of every cell in the heart would be impractical for implementation, e.g., on a modern desktop computer.

SUMMARY OF THE DISCLOSURE

As noted above, the present invention relates to apparatus and methods for simulating the activity of the heart and, in preferred embodiments, for simulating and testing effects of medical treatments on the heart. A simulation system includes and operates with a computer controlled heart model for generating and displaying simulated electrogram signals, representing the activity of a heart. To accomplish this task, preferred embodiments of the simulation system include various hardware components and software designed to realize a heart model and generate electrogram display data to display on an easily readable and user-friendly display format.

Preferred embodiments of the present invention comprise a computer-controlled model of the heart based on the relatively simple electrical characteristics of individual cells of the heart. The present inventors have recognized that groups of cells (tissue groups) of the heart can be selected such that the electrical characteristics of the tissue group as a whole resembles the simple electrical characteristic of an individual cell. If the number of tissue groups is small enough, a model of the heart, based upon such tissue groups is implementable with the computing power of an ordinary desktop computer.

Each tissue grouping in the model is associated with three timers: (1) a waiting to conduct timer; (2) a conducting timer; and (3) a refractory timer. In preferred embodiments, the management of the multiple timers for a tissue groupings model is implemented in a manner suitable for the computing power of a typical desktop computer. This may be accomplished, for example, by arranging a timer list containing data entries representing timer block values, and employing a software implemented routine for examining the timer list entries in an efficient manner. In a preferred arrangement, a doubly-linked list is managed as the timer list. The list is ordered such that the timer scheduled to expire the soonest is at the tail of the list. Conversely, the timer to expire the furthest into the future is toward the head of the list. Consequently, the heart model's timer check routine need only examine the last entry (or second to the last entry as discussed below) in the timer list to determine if any of the timers has expired. This significantly reduces the amount of computation required to check stimulation timer block status compared to other timing mechanism.

BRIEF DESCRIPTION OF THE DRAWINGS:

The detailed description will be made with reference to the accompanying drawings, wherein like numerals designate corresponding parts in the several figures.

FIGS. 6(a) through (e) are state diagrams or state machines for simulating states of tissue groupings, according to an embodiment of the present invention.

DETAILED DESCRIPTION OF PREFERRED EMBODIMENTS

The following detailed description is of the best presently contemplated mode of carrying out the invention. This description is not to be taken in a limiting sense, but is made merely for the purpose of illustrating the general principles of embodiments of the invention. The scope of the invention is best defined by the appended claims.

As discussed in more detail below, apparatus end methods according preferred embodiments of the present invention model the heart in groupings of cells, referred to as tissue groups. The present inventors have recognized that cells of the heart may be grouped according to their electrical and timing characteristics and that, each tissue groupings can be simulated relatively accurately, for example, with the computing power of a typical desktop computer. As a result, electrical activities of the heart can be simulated in a much more accurate and versatile manner than prior systems discussed above.

According to a preferred embodiment of the present invention, a simulation system includes and operates with a computer controlled heart model for generating and displaying simulated electrogram signals, representing the activity of a heart. To accomplish this task, preferred embodiments of the simulation system include various hardware components and software designed to realize a heart model and generate electrogram display data to display on an easily readable and user-friendly display format.

Figure 3:
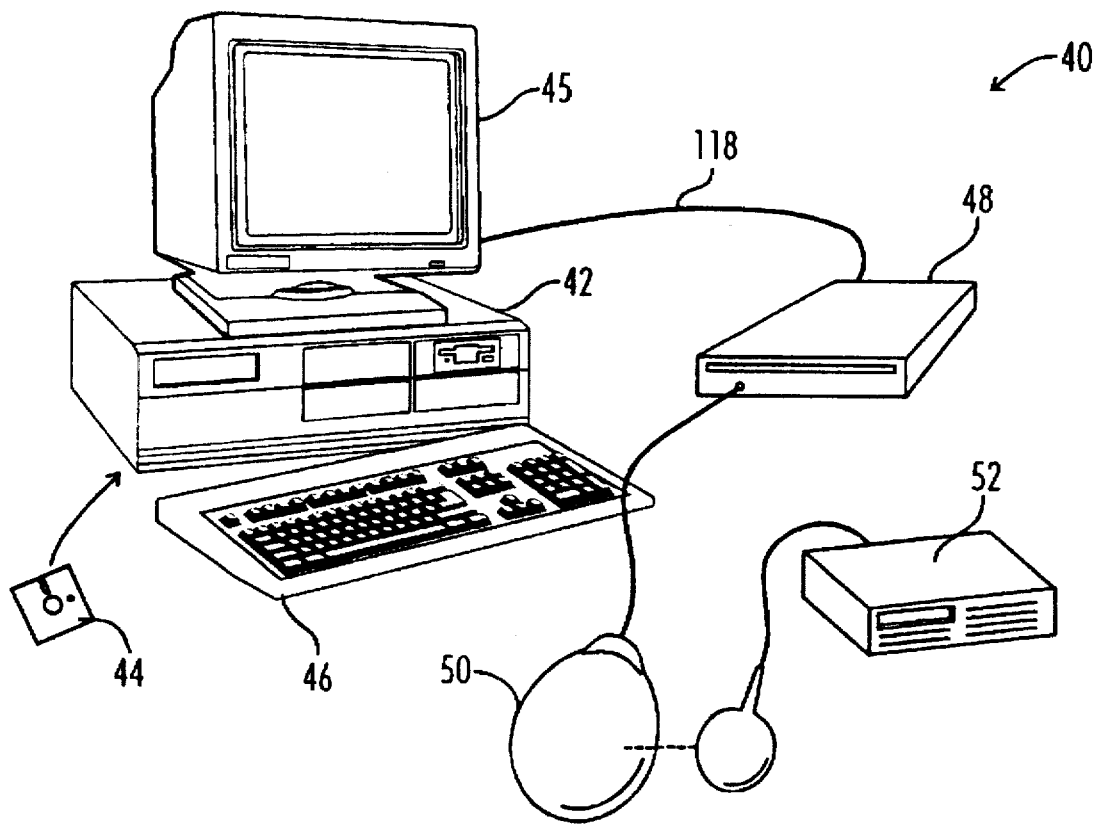
FIG. 3 is a schematic representation of a simulation system and related devices according to an embodiment of the present invention.

A simulation system and related devices according to an embodiment of the present invention is generally represented by the schematic drawing shown in FIG. 3. Referring to FIG. 3, the illustrated simulation system 40 includes a host processor device 42, such as a typical desktop computer which operates with host software represented by floppy disk 44 (however, it will be understood that the host software may be stored on any suitable storage medium, including, but not limited to, hard disks, compact disks, digital recording tape, RAM or ROM chips or the like). The computer 42 includes a display device 45 (such as a CRT device, an LCD device, or the like) and a user operated data input device 46 (such as a keyboard, touch screen, or the like). An implantable pulse generator interface (IPGIF) pod 48 is coupled to the computer 42 via any suitable electrical coupling, preferably an RS-232 link. A pacemaker 50 is coupled to the IPGIF pod, via an electrical or optical conductor suitable for transmitting pacemaker stimulation signals to the IPGIF pod (usually made of modified pacemaker leads). In preferred embodiments, the pacemaker is programmable, via a programming unit 52.

The simulation system 40 shown in FIG. 3 operates with a computer controlled heart model system which responds to data from various sources, including the user data input device 46 and the pacemaker 50, and generates display data for a display of electrogram signals simulating heart activity. The intercommunication of data involved in the operation of the system can be generally represented by the block diagram of a heart model system shown in FIG. 4, wherein various functions (such as display functions, data input functions and pacemaker signal input functions) are provided by dedicated modules and wherein characteristics of heart tissue groups and a pacemaker are simulated with the use of computer controlled models (such as a heart model and a pacemaker model).

In general, communications among modules and models is controlled by a dispatcher 54, which provides the timing synchronization and distribution across all modules within the simulator and provides synchronization delays as appropriate for the amount of time that has elapsed since the heart model was last called. The heart model system includes a heart model 56 which is based on tissue groupings, as described in more detail below. An input/output (I/O) module 58 allows the user to enter data, such as parameter information (e.g., via the user input device 46 shown in FIG. 3) to modify the underlying heart parameters (i.e. underlying rhythm, rate, refractory time etc.) as well as retrieve the current values of the heart model. A display module 60 receives signals 61 indicating wave onsets produced from within the heart's tissue groups (e.g. p-wave onset).

A leads module 62 provides signals 63 indicating that a captured pacing spike has occurred from either an actual implantable pulse generator IPC attached to the IPGIF pod or the simulated pacemaker model. The leads module 62 acts as an interface to the heart model for either an IPG 64 or a simulated pacemaker (e.g., a pacemaker model 66). The heart model provides signals 65 to the leads module representing electrogram events that occur within the atrium and ventricle. In response, the leads module provides signals 67 to inform the appropriate pacemaker (IPG or simulated) of the event. An additional communication link is shown between the leads and the display module, for signals 69 representing a non-captured spike communicated to the display module, for any pacing event that does not meet the strength-duration curve criterion for capture as discussed below.

As noted above, the heart model system shown in FIG. 4 includes a heart model 56. The heart model 56 comprises a model for simulating the electrical and timing characteristics of groups of cells of the heart (or tissue groupings). To better understand a simulation model based on the electrical and timing characteristics of tissue groupings, it is helpful to consider a simulation model based on certain electrical and timing characteristics of each individual cell of the heart. From a simulation perspective, characteristics of interest about an individual cell are that each cell:

is capable of being paced or stimulated from an adjacent cell;
is capable of conducting to, and stimulating an adjacent cell;
is capable of pacing spontaneously;
has a conduction rate characteristic;
has a repolarization rate, or refractory characteristic; and
has an intrinsic pacing rate characteristic.

With this relatively simplified approach, a cell would appear to have three potential states: polarized (ready to conduct or pace); conducting; and repolarizing (refractory). Thus, a model simulating each cell would include data processing and memory devices for tracking the state of each cell (e.g., by storing state data representing the state of each cell in an addressable memory location) and determining whether internal or external events result in a change of state of each cell (e.g., compare data representing an event with a stored table of actions or state changes associated with each event for each cell state of each cell). The storage requirements for storing cell state data and table data for every cell of the heart, and the processing requirements for processing such data, would be enormous.

The data processor would be required to determine, for each cell, the current cell state and to alter data corresponding to the cell state based on interactions with adjacent cells, electrical and timing characteristics of the cell and internal and external events. For example, a polarized cell can be stimulated from any adjacent cell, or from an external event, such as a stimulation pulse from a pacemaker lead, which will then cause it to go into the conducting state. Expiration of the intrinsic pacing rate timer can also cause the cell to go into the conducting state. However, if the intrinsic pacing rate of a cell is zero, the cell will not spontaneously depolarize during electrical diastole.

Consider, for example, a first cell in the conducting state. The first cell remains in the conducting state until its conduction rate timer has expired. When the timer expires, the cells adjacent the first cell are stimulated, and the first cell enters a repolarization state. For simulation purposes, it is assumed that further stimulation of the first cell during the conduction state has no additional effect on that cell.

The first cell remains in the repolarization state until its repolarization rate timer has expired, whereupon it enters the polarized state. Alternatively, the first cell, when in the repolarization state, can be stimulated to go directly into the conducting state by high potential electrical activity. The level of electrical activity required to cause this is a function of the amount of time that the cell has been in the repolarization state prior to the stimulation event. For many simulation purposes, this phenomenon can be ignored. However, advanced simulation systems may take into account the effects of this high potential stimulation activity.

Based on the above principles, a state chart or table for a cell would appear as follows:

| CURRENT STATE | TIME OUT EVENT | PACE STIMULUS | POST STIMULUS | NOTES |
| --- | --- | --- | --- | --- |
| POLARIZED | GOTO CONDUCTING | GOTO CONDUCTING | GOTO CONDUCTING | |
| CONDUCTING | GOTO REPOLARIZING | x | x | STIMULATE ADJACENT CELLS |
| REPOLARIZING | GOTO POLARIZED | x | GOTO CONDUCTING | |

Theoretically, a computer may be programmed to process and store data, as discussed above, such that data representing the current state of each cell could be stored in an addressable memory location, and data representing the occurrence of events (such as the expiration of a timer, a pace stimulus or a post stimulus) could be processed to result in a change of the current state or stimulation of adjacent cells, as outlined in the above table. However, since it is computationally impractical to simulate each and every individual cell in the heart with the power of a typical desktop computer, some other approach must be explored. If the number of cells simulated is reduced by 50%, the computational load is also reduced by 50%. After this simple refinement, each cell in the simulation represents two cells. Since the cells are of a very small physical size and nearly identical, this refinement would likely yield an electrical model with results that closely approximate the "all cells" model.

Unfortunately, the number of cells in this refined model is still too high for practical implementation. Accordingly, one may consider reducing the number of cells in the model by 50% once again and assessing whether or not there is sufficient computational power to simulate the remaining cells. One may consider repeating this process until the number of cells remaining in the model is suitable for the available computational power. However, the model will likely fall apart long before one reaches a practical number of cells for management by typical desktop computers, due to insufficient cells to provide the functionality required for the simulation. This occurs because the granularity of the model would be too coarse to produce a reasonable simulation.

Since the multi-cell refinements to the model break down prior to the time that it becomes feasible to run on a desktop computer with acceptable results, there is a need in the field for refinements of a more advanced nature to allow a simulation to run on cost-effective equipment.

Because many of the cells of the heart have similar timing and electrical characteristics as their adjacent neighboring cells, the present inventors have recognized that cells can be simulated as groups of cells (or tissue groupings), for example, based on their electrical and timing characteristics. Thus, a group of cells having similar electrical and timing characteristics may be simulated as a tissue grouping having electrical and timing characteristics dependent upon and resembling that of the type of cells in the group. A heart model, based on multiple tissue groupings, can then be simulated by simulating the electrical and timing characteristics and interactions of the tissue groupings, rather than individual cells. The number of tissue groupings for a heart model may be selected so as to allow simulations to be conducted with the computational power of a typical desktop computer.

Conceptually, the tissue grouping process can complicate the model somewhat. Because the model simulates group activities, it must now account for certain additional "group" characteristics. For example, a model based on tissue groupings must account for the conduction direction. With a model based on individual cells, conduction is to all adjacent cells and conduction direction is not a relevant concept. However, when simulating tissue groupings, it is necessary to distinguish between antegrade and retrograde conduction patterns. In particular, it is necessary to know what end of the connection to stimulate when a wave reaches the end of its conduction period.

Also, with a model based on individual cells, an electrogram is derived by the conduction patterns of all of the cells within a tissue over time and it is not necessary to know the electrogram characteristics of the tissue itself. With the tissue groupings model, however, the surface lead ECG pattern is a function of the electrogram characteristics of all of the tissues being simulated. The tissue electrograms are derivatives of what the individual cells in the model would have produced had they been simulated individually. Since these cells are not simulated, the electrograms are computed or produced algorithmically.

A tissue groupings model must account for the stimulation focus. With a model based on individual cells, only adjacent cells can be stimulated. Conceptually, with the tissue model, only adjacent tissue can be stimulated. Thus, the model must account for tissue groupings that are electrically adjacent the stimulation focus, A tissue groupings model should also account for stimulation that can occur in the center of a tissue conduction system, For example, if one of the tissue groupings chosen is the ventricular myocardial tissue, it could be very difficult to simulate multi-focal ventricular events.

A tissue groupings model must also account for propagation delays within the tissue. In the physical world, a small amount of time is required for a stimulus to propagate through a group of cells (forming a tissue grouping) on to another set of cells. To accurately simulate this phenomenon, a characteristic delay may be added between tissue groupings.

The problem of conduction direction can be largely eliminated by using tissue groupings that ensure that the conduction times through a tissue is shorter than the repolarization time of the adjacent stimulating tissue. In fact, this is the mechanism that occurs within the individual cell model as illustrated in FIG. 2(a).

Figure 2A:
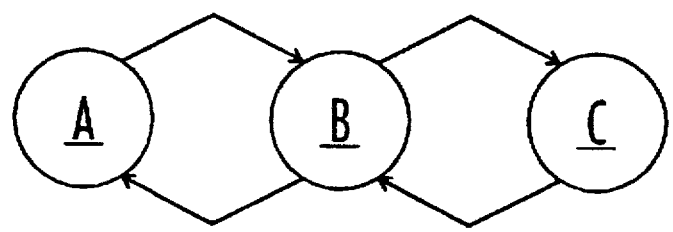
FIG. 2(a) is a simplified diagram of the cell to cell conduction pattern of adjacent cells A, B and C.

FIG. 2(a) is a simplified diagram of the cell to cell conduction pattern of adjacent cells A, B and C, with all cells initially in the polarized state: Consider a situation where cell A is stimulated into a conduction state. At the end of the conduction period, cell A stimulates its only adjacent cell B and enters the repolarization state. Cell B conducts, and at the end of its conduction period, stimulates adjacent cells A and C, and enters the repolarization state. Cell C then enters the conduction state, and cell A ignores the stimulation because it is still in repolarization. The net result of this conduction is a stimulated antegrade conduction (assuming, of course, that the normal conduction flow is from A to C).

The problem of producing complex electrograms is addressed by setting up tissue groupings that are small enough that the aggregate electrogram of the individual cells in the group is still relatively simple. For example, the electrogram of all cells in the ventricular myocardial tissue is quite complex as an aggregate. If, however, the ventricles were to be broken up into many tissue groupings (perhaps as many as a dozen, or so) the resulting individual electrograms would have much simpler waveforms. This is convenient, because the problem of how to simulate multi-focal activity within a particular tissue type is also addressed by breaking up that tissue into small tissue groupings, and allowing multi-focal activity to occur within the subgroups.

Based on these observations, a more idealized model can be accomplished by setting up "state machines" for subtissue groupings that operate in a very simplistic manner. If the proper subtissue groupings are chosen, these state machines will appear to be much like the state machine described for the single cell model.

The selection of subtissue groupings is dependent upon the end use of the model. For example, if the model is to be used simply to demonstrate normal sinus, 1st, 2nd and 3rd degree block rhythms, the only tissue groupings required are the atrium, the ventricle, and a conduction path. This is true because the only physiological events of interest for these cardiac rhythms (as far as a simulator is concerned) are the timing relationships between the atrial and ventricular depolarizations. Regardless of the timing among these tissues, each tissue generates only one representative electrogram. In particular, the atrium generates a classical P-wave, the ventricle generates a classical QRS-wave, and the conduction path generates no wave (as seen by an ECG lead). The only variable factor involved in each of these cardiac rhythms is the conduction time from the atrium to the ventricle. This factor can be varied, e.g., through the I/O module 58 (FIG. 4) in response to data entered by a user via input device 46 (FIG. 3).

Figure 1:
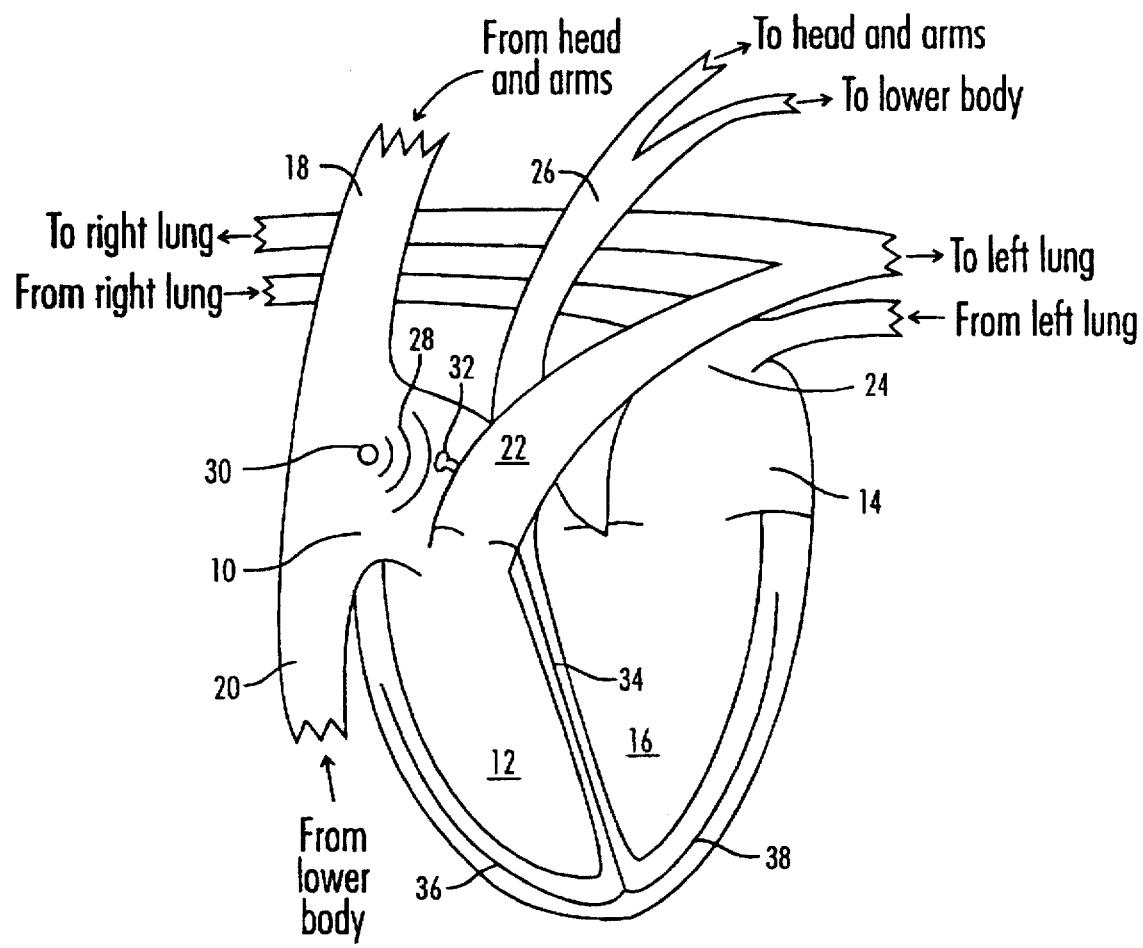
FIG. 1 shows a simplified drawing of a heart.
Figure 2:
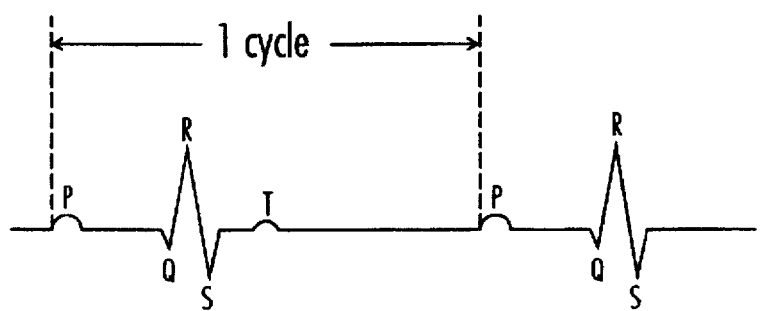
FIG. 2 is a simplified graph of a typical cardiac waveform.

This simple three tissue model, however, is not suited for simulating certain pathologies. For example, "narrow" and "wide" QRS complexes are used as clues to the pathology causing the arrhythmia. To simulate these conditions properly, it is necessary to break the model into more specific tissue groupings. In this case, more of the conduction pathway tissues must be simulated, including the SA node, the His Bundle and the left and right bundle branches. In addition, both the left and right ventricle would have to be simulated to automatically produce the proper variation in the QRS waveform. Accordingly, embodiments of the present invention include heart models formed of tissue groupings selected to allow simulations of pathologies involving conduction pathway tissues, such as the SA node 30, the Mit, the AV node 32, the His Bundle 34, the bundle branches 36 and 38 and the ventricles 12 and 16, with reference to FIG. 1.

Further embodiments of the present invention are capable of simulating sinus node pacemaker dysfunction and abnormalities of the sino-atrial conduction system. These pathologies may result in cardiac arrhythmias, such as sinus bradycardia, alternating brady- and tachyarrhythmias, sinoatrial block and/or sinus arrest. For example, a heart model embodiment for such simulations may have five tissue groupings comprising the S-A node group, the atrial conduction system group, the A-V node group, the His Bundle group, and the ventricular myocardium group.

Figure 4:
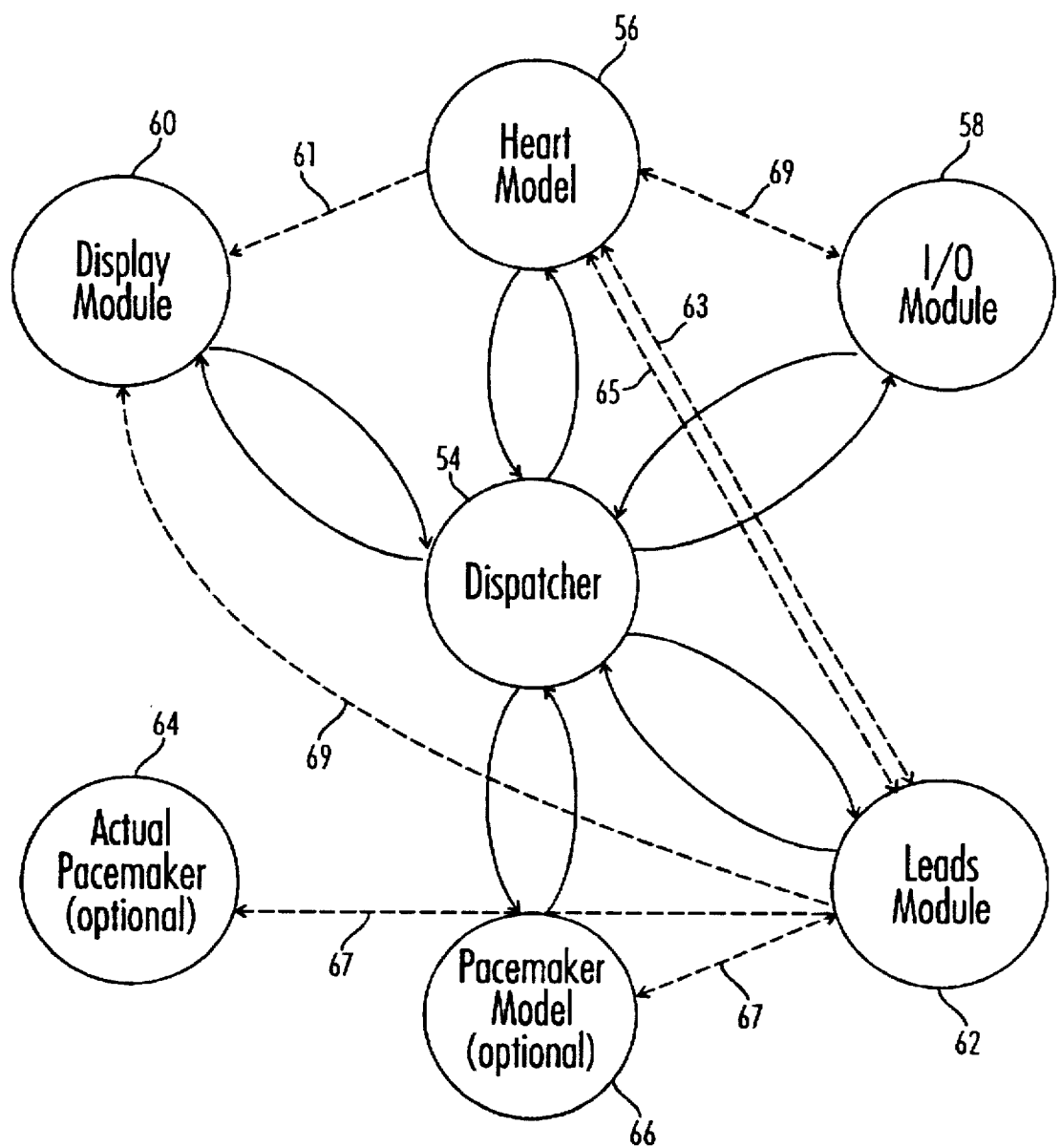
FIG. 4 is a block diagram of a heart model system according to an embodiment of the present invention.

In this five tissue grouping model embodiment, sinus bradycardia, tachycardia, and arrest are simulated by changing the intrinsic pacing rate of the SA node (e.g., via the input device 46 shown in FIG. 3 and the I/O module 58 shown in FIG. 4). A sinoatrial block exists when (1) the P-wave abruptly doubles or halves, indicating a 2:1 exit block from the pacemaker or (2) the P-wave rate progressively shortens culminating in a long P—P interval. Both of these sinoatrial block conditions are simulated by altering the SA node conduction time parameter, e.g., via the input device 46 (FIG. 3) and the I/O module 58 (FIG. 4).

Figure 5:
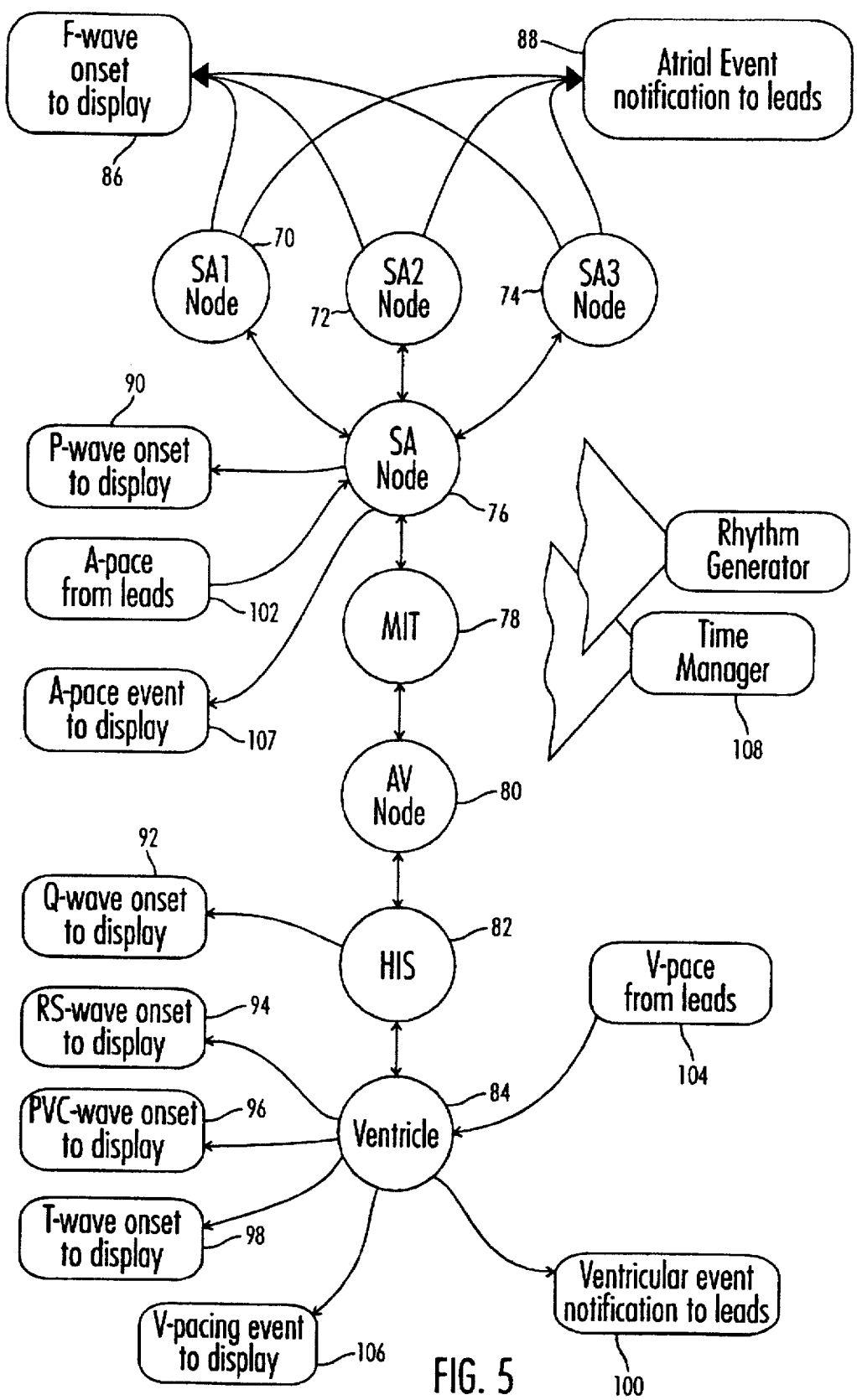
FIG. 5 is a simplified diagram of a seven tissue grouping model according to an embodiment of the present invention.

As should be apparent from the three tissue groupings model and five tissue groupings model discussed above, the subtissue groupings selected for the model are dependent upon the end use of the model (i.e., dependent upon the characteristics and pathologies to be simulated with the model). For example, a heart model embodiment capable of simulating atrial fibrillation may include ectopic tissue groupings, as shown in the seven tissue grouping model of FIG. 5. The diagram in FIG. 5 represents the interaction between tissue groupings and between the tissue grouping model and other components of the model system shown in FIG. 4. It will be understood that tissue grouping models composed of other selected combinations of tissue groupings could be similarly diagramed and simulated.

The seven tissue groupings model of FIG. 5 is composed of the following tissue groupings:

Ectopic Sino-atria node 1 (SA1), represented by reference character 70;

Ectopic Sino-atria node 2 (SA2), represented by reference character 72;

Ectopic Sino-atria node 3 (SA3), represented by reference character 74;

Sino-atria node (SA node), represented by reference character 76;

Middle Intermodel Tract (MIT), represented by reference character 78;

Atrial-Ventricular node (AV node), represented by reference character 80;

Bundle of HIS (HIS), represented by reference character 82;

Ventricle, represented by reference character 84.

The double arrow lines in FIG. 5 represent conduction interactions between tissue groupings. FIG. 5 shows a conduction interaction between the SA node 76 and the adjacent SA1, SA2 and SA3 nodes 70–74. This allows the simulation of atrial fibrillation, by allowing the ectopic tissue groupings to erratically stimulate the SA node.

As any one or combination of ectopic tissue groupings are stimulated, the model signals the display module 60 (FIG. 4) of an F-wave onset, as shown at 86. In addition, the model signals the leads module 62 (FIG. 4) of an atrial event, as shown at 88. At the end of the conduction period of the stimulated ectopic tissue groupings, the SA node is stimulated, as shown by the conduction interaction arrow between the SA node 76 and the ectopic tissue groupings 72, 74 and 76. As the SA node is stimulated, the model signals the display module 60 (FIG. 4) of a P-wave onset, as shown at 90.

The conduction of the stimulus continues through the MIT 78, AV node 80, bundle of HIS tissue groups 82 and finally reaches and stimulates the ventricle tissue group 84. As the His bundle is stimulated, the model signals the display module 60 (FIG. 4) of a Q-wave onset, as shown at 92. As the ventricle is stimulated, the model signals the display module 60 of an RS-wave onset, as shown at 94. The model signals the display module 60 of a PVC-wave onset, as shown at 96, upon the ectopic stimulation of the ventricle. As the ventricle goes into a repolarization or refractory state (e.g., at the expiration of the ventricle conduction rate timer), the model signals the display module of a T-wave onset, as shown at 98. In addition, the model signals the leads module 62 (FIG. 4) of a ventricular event, as shown at 100.

As a result, a simulated complete P-QRS-T ECG wave complex may be built up and integrated into the appropriate waveform, as each individual wave component is generated by the corresponding tissue group. In addition, preferred embodiments respond to externally paced event (IPG or simulated pacemaker). The leads module 62 (FIG. 4) signals the heart model of an A-pace or a V-pace, as shown at 102 and 104. The model signals the display module 60 (FIG. 4) of pacing events, such as shown at 106 and 107.

As apparent from the above description of the model shown in FIG. 5, the model signals the display module 60 (FIG. 4) of wave onsets and pacing events, by simulating the conduction of a stimulus along the tissue groupings of the model. By modeling the characteristics of each tissue grouping after the individual cell model discussed above, the conduction of a stimulus through the tissue groupings can be simulated by simulating timing functions and conduction states for each tissue grouping, similar to the simulation of timing and conduction states discussed above for each cell of the individual cell model.

The conduction state transitions for each tissue grouping are controlled by the model, in response to expirations of timers and occurrences of other events, as shown in the state diagrams or state machines of the above-described seven tissue grouping model in FIGS. 6(a) through 6(e). The software and hardware implementation of such state machines will be readily realizable by the skilled artisan.

The diagrams shown in FIGS. 6(a) through 6(e) illustrate that each tissue grouping can take one of only 3 states at any instant in time. This follows directly from the individual cell model discussed above. A transition from one state to the next is a direct result of a particular event that has occurred within or outside of the heart model itself. The arrows represent a transition from the current state to another state. The adjacent text describes the event that must occur in order to cause this state transition. During the state transition, a specific response or action occurs. Each tissue group responds with a specific action based on its current state and the current event.

The events, state transitions and other actions for each tissue grouping shown in the diagrams of FIGS. 6(a) through 6(e) are further illustrated in the charts below. These charts include a source column for specifying the source of an event, an event column for specifying the event generated by the source, an action column specifying the response resulting from the event and the current state of the tissue grouping, and a recipient column for specifying the entity (inside or outside the heart model) to receive a response or action. A source can be an entity within the heart model system (e.g., another tissue group) or outside the module (e.g., the leads module 62 in FIG. 4).

SA NODE MODEL COMPONENT

| SOURCE | EVENT | ACTION | RECIPIENT |
|---|---|---|---|
| SA Node tissue group | waiting to conduct timer timeout | output atrial agram notification | LEADS module |
|  |  | output p-wave onset notification | ECG DISPLAY module |
| MIT tissue group | retrograde stimuli | output p-wave onset notification | ECG DISPLAY module |
| SSA1, SA2 and SA3 tissue group | ectopic stimuli | output p-wave onset notification | ECG DISPLAY module |
| SA Node tissue group | conduction timer timeout | stimulate adjacent tissue group (antegrade stimulation) | MIT tissue group |
| SA Node tissue group | refractory timer timeout | nothing (null) | none |
| LEADS module | atrial pace | output atrial egram notification | LEADS module |
|  |  | output paced p-wave onset notification | ECG DISPLAY |

MIT MODEL COMPONENT

| SOURCE | EVENT | ACTION | RECIPIENT |
|---|---|---|---|
| MIT tissue group | waiting to conduct timer timeout | none (null) | none |
| SA Node tissue group | antegrade stimuli | none | none |
| AV Node tissue group | retrograde stimuli | none | none |
| MIT tissue group | conduction timer timeout | stumilate adjacent tissue group (antegrade or retrograde stimulation) | AV Node tissue group or SA Node tissue group |
| MIT tissue group | refractory timer timeout | none | none |

AV NODE MODEL COMPONENT

| SOURCE | EVENT | ACTION | RECIPIENT |
|---|---|---|---|
| AV Node tissue group | waiting to conduct timer timeout | none | none |
| MIT tissue group | antegrade stimuli | none | none |
| HIS tissue group | retrograde stimuli | none | none |
| AV Node tissue group | conduction timer timeout | stumilate adjacent tissue group (antegrade or retrograde stimulation) | MIT tissue group or HIS tissue group |
| AV Node tissue group | refractory timer timeout | none | none |

| HIS MODEL COMPONENT | | | |
|---|---|---|---|
| SOURCE | EVENT | ACTION | RECIPIENT |
| HIS tissue group | waiting to conduct timer timeout | output q-wave onset notification | ECG DISPLAY |
| AV Node tissue group | antegrade stimuli | output q-wave onset notification | " |
| Ventricle tissue group | retrograde stimuli | output q-wave onset notification | " |
| HIS tissue group | conduction timer timeout | stimulate adjacent tissue group (antegrade or retrograde stimulation) | Ventricle tissue group or AV Node tissue group |
| HIS tissue group | refractory timer timeout | none | none |

| VENTRICLE MODEL COMPONENT | | | |
|---|---|---|---|
| SOURCE | EVENT | ACTION | RECIPIENT |
| Ventricle tissue group | waiting to conduct timer timeout | output ventricular egram notification | LEADS module |
| | | output rs-wave onset notification | ECG DISPLAY |
| HIS tissue group | antegrade stimuli | output rs-wave onset notification | " |
| Ventricle tissue group | conduction timer timeout | stimulate adjacent tissue group (retrograde stimulation, if paced) | HIS tissue group |
| | | output t-wave onset notification | ECG DISPLAY |
| Ventricle tissue group | refractory timer timeout | none | none |
| LEADS module | ventricular pace | output ventricular egram notification | LEADS module |
| | | output t-wave onset notification | ECG DISPLAY |
| | | start retrograde | Ventricle tissue group |

Each tissue group operates with three timers, comprising: (1) a waiting to conduct timer, (2) a conducting timer and (3) a refractory timer. In preferred embodiments, the timers are controlled by a timer manager 108 (FIG. 5) in a table data structure. For example, the timer manager may be composed of a timer block (addressable memory) for each timer of each tissue grouping in the model, and at least one clock. Each timer block contains the current timer value, the initialization value, and a timeout flag indicating whether or not a timer has expired. A timer block is loaded with the count that represents when the timer will expire, either as a software implemented initialization procedure or by the user, e.g., via the input device 46 (FIG. 3). The clock provides a count (either by counting up from a predetermined value for comparison with the preloaded expiration count or by counting down from the preloaded expiration count) for updating the current timer value component of the timer block.

In preferred embodiments, the management of the multiple timers for a tissue groupings model is implemented in a manner suitable for the computing power of a typical desktop computer. This may be accomplished, for example, by arranging a timer list containing data entries representing timer block values, and employing a software implemented routine for examining the timer list entries in an efficient manner. In a preferred arrangement, a doubly-linked list is managed as the timer list. The list is ordered such that the timer scheduled to expire the soonest is at the tail of the list. Conversely, the timer to expire the furthest into the future is toward the head of the list. Consequently, the heart model's timer check routine need only examine the last entry (or second to the last entry as discussed below) in the timer list to determine if any of the timers has expired. This significantly reduces the amount of computation required to check stimulation timer block status compared to other timing mechanisms. On average, the heart model performs very little work due to the passage of a time tick interval since model timers are normally either running or idle and a timer expired condition is statistically infrequent.

An embodiment of single element, doubly linked timer list with timer (n), is represented by the following chart:

| HEAD POINTER | | TAIL POINTER |
|---|---|---|
| forward-pointer→ ←back pointer timer - 32767 int. val to_flag | forward-pointer→ ←back-pointer timer - (n) init. val to_flag | forward-pointer→ ←back-pointer timer - 0 init. val to_flag |

A head pointer variable points to the first timer block in the list. This particular block is a reserved block and has been assigned a timer value 32767 to represent a timer that will never expire. The tail pointer variable points to the last timer block in the list. This block is also a reserved block and has been assigned a timer value of 0. A timer block that is to be added to the timing block list will be added such that its calculated expiration time t1 is less than the preceding blocks expiration time t2, and greater than the succeeding block's expiration time t0. This scheme is used to simplify the linking primitive operation where timer items are added, deleted, and examined. Using these reserved header and trailer block values avoids having to check whether or not each timer has expired and whether or not any exceptions apply. If a timer value of 0 is to be entered as a current timer value on the linked list, the timer value is forced to be 1 to prevent the ambiguous condition of appearing like the reserved last block in the list. When a timer expires, the timeout flag (to_flag) is set to TRUE.

Figure 7:
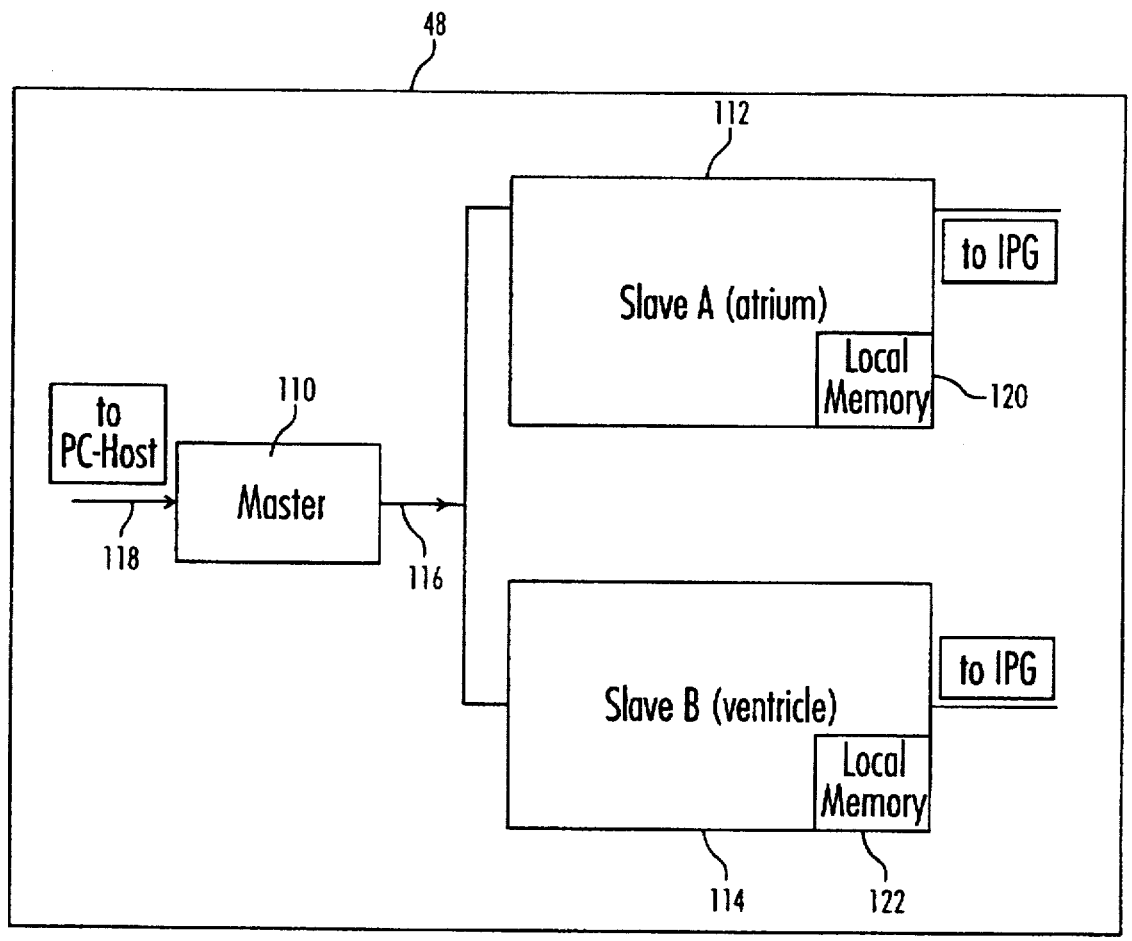
FIG. 7 is a block diagram representing the general configuration of an IPGIF pod according to an embodiment of the invention.

A timer list scheme as discussed above for managing the timers of a heart model and the implementation of the heart model based on tissue groupings having electrical and timing characteristics similar to that of individual cells, allows the simulation of relatively complex heart activity while minimizing the computational power necessary for the simulation. As discussed above, preferred embodiments of the invention also simulate and/or respond to pacemaker activity, via the IPGIF interface pod 48 (FIG. 3) between a pacemaker (IPG or simulated) and other components of the model system A block diagram representing the general configuration of an IPGIF pod 48 according to an embodiment of the invention is shown in FIG. 7. The IPGIF pod 48 includes three main processor boards, comprising the master processor board 110, the atrial slave processor board 112 and the ventricular slave processor board 114. The master processor board 110 includes a data processor (for example a microprocessor) capable of communicating to either slave processor board via the slave data bus 116. Preferably, this is accomplished through an addressing scheme that also allows additional slave processor boards to be added for expansion, including. For example, the master processor selects the specific slave via a unique address which is placed on the bus 116.

The master processor board 110 also communicates directly to the host computer 42 (FIG. 3) over the electrical link 118, preferably an RS-232 data link. For example, the master processor board 110 communicates pacing events that occur in either slave processor board to the host computer 42. It also communicates artifact events that occur in the host computer to the appropriate slave.

The master processor board 110 operates in two modes: command mode and artifact mode. In a command mode, the master processor board is capable of accepting commands from the host computer and to act upon them accordingly. In general, command mode is entered to download code and/or data. The downloaded code may be the actual run-time software that is executed following a bootup of the host computer, for all processors in the IPGIF pod. Downloaded data may be, for example, tables and wave patterns that characterize a particular patient's physiology to be simulated by the model. These characteristics include atrial and ventricular electrogram waveforms and atrial and ventricular strength duration curves (tables). The master processor passes these waveforms and tables to the appropriate slave processor board, via bus 116.

The artifact mode is entered following system code initialization, downloading of endocardial waveforms, and downloading of tables. This is the mode in which simulation occurs. In this mode, real-time data is passed between the host computer 42 (FIG. 3) and the master processor 110, and between the master processor and either slave processor. The host computer 42 notifies the master processor when the heart's atrium or ventricle tissue group has depolarized (contracted) in the model, as represented by signals 90 and 94 in FIG. 5. This notification, labeled as p-onset and rs-onset respectively, is passed on to the atrial or ventricular slave processor board respectively. The slave processor board activates a process to present the heart's endocardial electrogram to the pacemaker. Preferably, the slave already has the electrogram waveform data in its local memory 120 or 122. As a result, the slave only requires a notification of a wave onset (which can be accomplished, for example, with a single byte of dam) from the master processor to begin emitting the actual electrogram to the pacemaker, via the digital to analog converter.

When the pacemaker stimulates the heart, the appropriate slave processor detects the stimuli and compares the amplitude and pulse width, for example, with a strength duration table stored in its local memory 120 or 122, to determine if, and when, capture should occur. The slave processor notifies the master 110 if a paced event has occurred. Capture notification is sent as soon as it occurs. The slave processor also determines the amplitude and pulse width, regardless of whether the stimuli is captured or not at the conclusion of the spike. The master processor 110 passes this pacing event information to the host computer 42 (FIG. 3) for processing by the heart model in the manner discussed above.

In preferred embodiments, an endocardial electrogram waveform may be created and stored in a suitable storage medium, such as the host computer disk digital tape, hard disk or other suitable storage medium. The user creates an electrogram using the electrogram editor with the host computer 42 (FIG. 3). The electrogram is stored as a disk file and can be retrieved by the host simulator software and transferred to the IPGIF pod 48, via the RS-232 link 118 (FIG. 7). A user may create multiple electrograms, for example two electrograms: one for the atrium and one for the ventricle, and attach them to a patient's physiological profile. The user similarly creates or retrieves appropriate strength duration curves and attaches them to a patient profile. The user then may download the electrograms and strength duration curves to the appropriate slaves processors in the IPGIF pod 48 (FIG. 3). Because the appropriate strength duration and electrogram data is stored locally in the slave processors 112 and 114, the slave processors are able to quickly process paced events (pacing spikes from the pacemaker) and depolarization events (onset notifications from the master processor 110).

Each slave processor may operate with a comparator for comparing each pace with a preset minimum amplitude threshold value and passing the pace to the slave processor only if the pace exceeds the preset minimum value. If a pacing spike is passed to the slave processor, the processor takes multiples samples and measurements of the amplitude of the spike, for example, sampling every 100 µS, and subsequently measures the pulse width. By comparison with the strength-duration curve stored locally in the slave processor, the IPGIF pod can provide the capture detection function and need only transmit a capture detect status signal to the host computer. Furthermore, only two bits are needed to describe the activity in each chamber (i.e. four bits total). From the two bits, four status conditions can be transmitted: Unipolar captured, Bipolar captured, Detected—Not captured and Not detected—Not captured. Once the pacing spike ends, the slave processor also sends data representing the pulse width and maximum amplitude to the host computer.

As a result, the amount of data required to be passed between the host computer and the IPGIF pod, over the RS-232 link 118 when a paced event occurs, can be minimized. In addition, the load on the host computer's central processing unit (CPU) may be eased so that the host computer's CPU may be more dedicated to the simulation of the heart and simulated pacemaker. If the host computer were to process each paced event, the IPGIF pod (which is sampling the pace amplitude, for example, every 100 uS) would be required to pass each sampled pace amplitude value to the host. For a 1.6 mS pulse width, this would amount to 16 data values. The host would be responsible for measuring the pulse width. Once a pulse width and amplitude is determined, the host would then determine if the pace was of sufficient energy for capture by referencing the strength duration table. The spike would then be determined to be either captured or non-captured. However, with the strength-duration (SD) table data and waveform data stored locally with the slave processors 112 and 114, according to preferred embodiments of the present invention, the capture and detection processing can be performed by the IPGIF pod, rather than the host computer. Furthermore, the IPGIF pod acts as a filter to avoid flooding the host stimulation processor with extraneous, non-captured pacing events and electrical noise.

Preferred embodiments of the invention minimize the amount of data that needs to be passed throughout the heart simulator system. Specifically, surface ECG waveform artifacts are integrated to represent various forms of the PQRST wave pattern. The PQRST wave is broken down into smaller stylized waveforms. Each of these waveforms contain a maximum number of data values, for example, 500 data values, with each value representing a period of time, for example, 1 mS, of an ECG. Each waveform fragment is a characteristic result of the electrical activity produced by a specific tissue grouping within the heart model, as discussed above. A copy of each waveform is used by the display module 60 (FIG. 4) as well as optionally downloaded to a secondary IPGIF pod. Each waveform is downloaded as a separate table from the host processor. As a result, during simulations, only signals representing the onset of a waveform (e.g., a p-wave onset 90, a q-wave onset 92, etc, as shown in FIG. 5) are provided to the display module 60 (FIG. 4), since the module already contains the needed wave artifact information in its own local tables. Once a waveform onset signal is received by the display module 60, the module integrates the wave data into its pending display array. This mechanism for sending only onset notifications can significantly reduce the amount of data transfer between the display module and the heart model, in the order of 500/1.

According to a further embodiment of the invention, an external ECG display or strip chart recorder is added to the heart simulator system. In the heart model system diagram of FIG. 4, this would be shown by a connection of the leads module 62 to an optional external IPGIF. In this instance, an ECG monitor is connected to an additional, optional IPGIF hardware pod that is used to generate the signals that mimic a surface ECG. The resulting surface ECG activity is displayed on the attached monitor. This is accomplished by downloading all of the stylized surface artifact waveforms to the IPGIF slave processor. For each wave onset notification, the host computer sends a single byte value to the IPGIF pod. This causes the associated artifact to be integrated into the pending artifact array, and subsequently to be generated via a digital to analog converter (DAC).

A table of artifact data comprises a byte indicating the length of the wave (in bytes), followed by the table which has been created in DAC counts. Each entry of the table represents a specific amplitude value for a period of time, for example 1 millisecond, relative to the onset of that particular artifact. Note that some artifact waveforms may have a zero amplitude for a significant period of time to account for the physiological delay of the ECG signal from the heart though the various tissues to the surface of the body (i.e. endocardiogram versus Surface ECG timing differences).

Preferably, the IPGIF pod supports both unipolar and bipolar pacing. The detection of unipolar or bipolar is performed automatically during each pacing event generated by the pacemaker. This is accompanied by monitoring of the presence of a pacing voltage across the case tip leads (unipolar) and the ring-tip leads (bipolar) concurrently. Once the configuration is determined, the slave processor encodes this event and passes the information to the master processor. The master processor subsequently passes it to the host computer and the ECG Display presents the unipolar or bipolar pacing artifact to the display module.

A strength duration curve is normally used to represent how the patients heart will respond to pacing at various energy levels. Preferably, it is represented by graph where the pacing pulse width is on the horizontal axis and the pacing amplitude in volts is on the vertical axis and a line is drawn representing the energy required to cause the heart to react to the stimuli presented by the pacemaker. To determine whether or not a pacing spike has been captured, the intersection of the pace amplitude and pulse width represents the electrical energy. All pacing energy that falls above the strength-duration line on the graph is determined to have been captured and any energy that falls below that line has not been captured. The direct mapping of this curve to a data table results in a two dimensional array with the column representing pulse width (time) and the rows the pulse amplitude (volts).

However, according to a further embodiment of the present invention, the S-D curve is compressed into a single-dimensioned array. This minimizes the required demand on the CPU and minimizes memory space. This array is indexed by the time delta relative to the onset of the pace event.

This approach uses the known impedance of the tissue to convert a Pulse-Width-as-a-function-of-Amplitude into an Energy-as-a-function-of-Pace-Time relationship. The energy required to cause capture is a product of the energy exerted by the IPG and the duration that it is exerted (i.e. Pulse Width). Furthermore, the energy of the pacing stimuli is a function of the pacing spike voltage and the impedance of the load. A function is then derived that converts the S-D curve into voltages, which is ultimately normalized into the actual ADC counts that are provided by the converter. This count table is what is actually downloaded for the IPGIF to use on a real-time basis.

The slave processor boards may include, for example, 8-bit micro-processors which use this array of data in the table to quickly compare each ADC count to the threshold required to indicate capture at regular time intervals corresponding to standard SD tables during the pacing event. The initial comparison is started by the slave processor whenever the pacing voltage rises above a pre-determined threshold. Conversely, comparison is stopped by the slave processors when the pace voltage falls below that pre-determined threshold. The compression of this data structure (1) minimizes the required CPU processing; (2) comes very little memory; and (3) results in an array that is uni-dimensional while retaining all of the information required to determine if, and when, a particular pacing spike is captured.

Further preferred embodiments of the invention perform load switching for the pacemaker's sensing and pacing modes. This is desirable since there is a large signal/small signal problem to overcome. The simulator presents a very small endocardial signal for the pacemaker to sense, but the pacemaker responds with a signal that is several orders of magnitude greater on the same leads. The interface must accurately generate the small signal, while retaining the ability to accurately measure and respond to the large signal.

According to a preferred embodiment, the IPGIF pod provides a switchable load impedance. While the pacemaker is sensing electrograms, the IPGIF pod presents a high load impedance to the pacer's sensing circuits. However, during the actual pacing spike, the IPGIF pod senses the spike onset and quickly switches in a different load impedance for the pacemaker to drive. When the spike is over, the IPGIF switches the heart load impedance back out and returns to the high impedance load suitable for the small signal generation.

Figure 8:
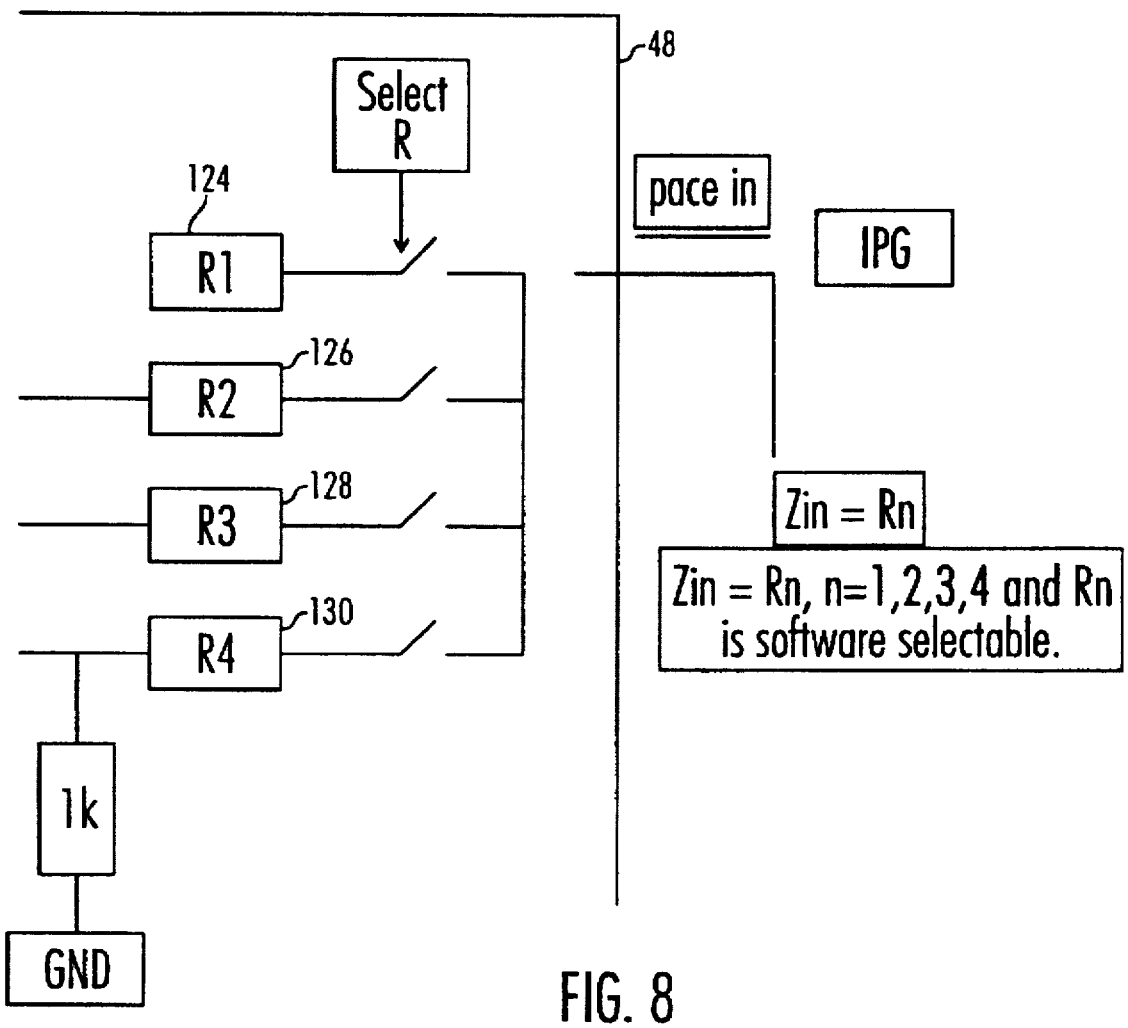
FIG. 8 shows a generalized representation of a load impedance switching circuit.

FIG. 8 shows a generalized representation of a load impedance switching circuit, comprising a plurality of resistors, for example, 4 software selectable resistor loads 124, 126, 128 and 130. There are 4 resistors, 2 for case-tip Unipolar) and 2 for ring-tip (Bipolar) pacing. This allows the user to select the designed heart impedance loads that the pacemaker is to see during pacing stimulus. A user may specify one of the four impedances to simulate various physiological conditions.

We claim:

1. A system for simulating an electrogram waveform of the activity of a plurality of heart tissue groupings, the system comprising:

a heart model composed of a plurality of processor controlled state machines for providing electrogram artifact signals; and a signal processor for composing an electrogram waveform from the electrogram artifact signals;

wherein each state machine corresponds to a respective tissue grouping of the heart;

wherein each state machine is switchable between three states, representing a polarized state, a conducting state and a repolarizing state of the corresponding tissue grouping;

wherein each state machine is associated with a timer having a preset time period for providing a timeout signal upon the expiration of the preset time period following the switch of the state machine into the state associated with the timer; and wherein at least two state machines of the heart model provide artifact signals corresponding to artifacts of an electrogram waveform.

2. A system as recited in claim 1, further comprising a display device for displaying said electrogram waveform.

3. A system as recited in claim 1, wherein each state machine comprises an addressable memory for storing a signal representing the state of the state machine.

4. A system as recited in claim 1, further comprising processor means responsive to the timeout signal of each state machine, for switching the state of the state machine.

5. A system as recited in claim 1, wherein each state machine timer is associated with an addressable memory block for storing data representing the expiration time of the timer.

6. A system as recited in claim 5, wherein said timer memory blocks are arranged in a timer list in a chronological order determined by the expiration time represented by the stored data, with the timer memory block storing the expiration time furtherest in the future arranged adjacent one end of the list and the timer memory block storing the expiration time nearest in the future arranged adjacent the opposite end of the list.

7. A system as recited in claim 1, further comprising means for providing a stimulation signal and wherein at least one state machine has means responsive to a stimulation signal for switching the state of the state machine.

8. A system as recited in claim 1, further comprising:

a pacing stimulation signal source for providing a pacing stimulation signal;

a pacing interface module coupled to receive the pacing stimulation signal, the pacing interface module having signal means for providing a pacing signal to the heart model, in response to selective pacing stimulation signals.

9. A system as recited in claim 8, wherein at least one state machine has means responsive to a said pacing signal for switching the state of the state machine.

10. A system as recited in claim 9, wherein the pacing stimulation signal comprises an electrical pulse signal having a maximum pulse amplitude and pulse width and wherein the pacing interface module comprises:

local memory for storing at least one strength duration table composed of data representing pulse amplitudes and pulse widths; and a processor for comparing the maximum amplitude and width of a pacing stimulation signal received from the pacing stimulation signal source with the strength duration table to determine whether the received pacing stimulation signal exceeds both amplitude and width characteristics represented by data of any table entry;

wherein said signal means comprises means for providing a pacing signal to the heart model in response to a received pacing stimulation signal that exceeds said amplitude and width characteristics represented by a table entry.

11. A system as recited in claim 10, wherein said pacing stimulation signal source comprises a pacemaker.

12. A system as recited in claim 11, wherein said pacing stimulation signal source comprises a signal generator for generating a simulated pacemaker pacing stimulation signal.

13. A system as recited in claim 1, further comprising:

a pacing stimulation signal source for providing atrial and ventricle pacing stimulation pulse signals, each of said pacing stimulation signals having a pulse width and a maximum pulse amplitude;

a pacing interface module coupled to receive the pacing stimulation signal, the pacing interface module having an atrial slave processor and a ventricle slave processor for processing atrial and ventricle pacing stimulation signals, respectively, and signal means for providing a pacing signal to the heart model, in response to selective pacing stimulation signals;

wherein each of said atrial and ventricle slave processors is associated with a respective memory for storing at least one strength duration table composed of data representing pulse amplitudes and pulse widths; and wherein said atrial slave processor comprises means for comparing the maximum amplitude and width of an atrial pacing stimulation pulse signal received from the pacing stimulation signal source with the strength duration table stored in the memory associated therewith to determine whether the received atrial pacing stimulation signal exceeds both amplitude and width characteristics represented by data of any table entry;

wherein said ventricle slave processor comprises means for comparing the maximum amplitude and width of an ventricle pacing stimulation pulse signal received from the pacing stimulation signal source with the strength duration table stored in the memory associated therewith to determine whether the received ventricle pacing stimulation signal exceeds both amplitude and width characteristics represented by data of any table entry;

wherein said signal means comprises means for providing an atrial pacing signal to the heart model in response to a received atrial pacing stimulation signal that exceeds said amplitude and width characteristics represented by a table entry in the memory associated with the atrial slave processor; and wherein said signal means comprises means for providing a ventricle pacing signal to the heart model in response to a received ventricle pacing stimulation signal that exceeds said amplitude and width characteristics represented by a table entry in the memory associated with the ventricle slave processor.

14. A system as recited in claim 13, wherein at least one state machine has means responsive to a said atrial pacing signal for switching the state of the state machine and wherein at least one state machine has means responsive to said ventricle pacing signal for switching the state of the state machine.

15. A system as recited in claim 14, further comprising processor means responsive to the timeout signal of each state machine, for switching the state of the state machine.

16. A system as recited in claim 15, wherein each state machine timer is associated with an addressable memory block for storing data representing the expiration time of the timer.

17. A system as recited in claim 16, wherein said timer memory blocks are arranged in a timer list in a chronological order determined by the expiration time represented by the stored data, with the timer memory block storing the expiration time furtherest in the future arranged adjacent one end of the list and the timer memory block storing the expiration time nearest in the future arranged adjacent the opposite end of the list.

18. A method of simulating an electrogram waveform of the activity of a heart, the method comprising the steps of:

defining a plurality of tissue groupings of the heart;

associating a respective processor controlled state machine with each defined heart tissue grouping, each processor controlled state machine being switchable between three states, representing a polarized state, a conducting state and a repolarizing state of the corresponding tissue grouping;

associating each state of each state machine with a timer having a preset time period for timing the expiration of the preset time period following a switch of the state machine into the state associated with the timer;

switching the state of each processor controlled state machine upon the expiration of the timer associated with the state of the state machine;

generating a first electrogram artifact signal with one of said processor controlled state machines, upon switching of said processor controlled state machines between two of said three states;

generating a second electrogram artifact signal with a second of said processor controlled state machines, upon switching of said second processor controlled state machines between two of said three states;

composing an electrogram waveform from the electrogram artifact signals; and displaying the electrogram waveform.

19. A method as recited in claim 18, further comprising the steps of:

providing a pacing stimulation signal from a pacing stimulation signal source;

coupling a pacing interface module to receive the pacing stimulation signal from the pacing stimulation signal source;

providing a pacing signal to the heart model, in response to selective pacing stimulation signals;

switching the state of at least one of said processor controlled state machine upon said pacing signal being provided to the heart model.

20. A method as recited in claim 18, further comprising the steps of:

providing atrial and ventricle pacing stimulation signals from a pacing stimulation signal source, each of said pacing stimulation signals having a pulse width and a maximum pulse amplitude;

coupling a pacing interface module to receive the atrial and ventricle pacing stimulation signals from the pacing stimulation signal source, the pacing interface module having an atrial slave processor and a ventricle slave processor for processing atrial and ventricle pacing stimulation signals, respectively;

associating each of said atrial and ventricle slave processors with a respective memory;

storing at least one strength duration table composed of data representing pulse amplitudes and pulse widths in each respective memory associated with the atrial and ventricle slave processors;

comparing the maximum amplitude and width of an atrial pacing stimulation pulse signal received from the pacing stimulation signal source with the strength duration table stored in the memory associated therewith to determine whether the received atrial pacing stimulation signal exceeds both amplitude and width characteristics represented by data of any table entry;

comparing the maximum amplitude and width of a ventricle pacing stimulation pulse signal received from the pacing stimulation signal source with the strength duration table stored in the memory associated therewith to determine whether the received ventricle pacing stimulation signal exceeds both amplitude and width characteristics represented by data of any table entry;

providing an atrial pacing signal to the heart model in response to a received atrial pacing stimulation signal that exceeds said amplitude and width characteristics represented by a table entry in the memory associated with the atrial slave processor;

providing a ventricle pacing signal to the heart model in response to a received ventricle pacing stimulation signal that exceeds said amplitude and width characteristics represented by a table entry in the memory associated with the ventricle slave processor; and switching the state of at least one of said processor controlled state machine upon said pacing signal being provided to the heart model.

wherein each of said atrial and ventricle slave processors is associated with a respective memory for storing at least one strength duration table composed of data representing pulse amplitudes and pulse widths; and wherein said atrial slave processor comprises means for comparing the maximum amplitude and width of an atrial pacing stimulation pulse signal received from the pacing stimulation signal source with the strength duration table stored in the memory associated therewith to determine whether the received atrial pacing stimulation signal exceeds both amplitude and width characteristics represented by data of any table entry;

wherein said ventricle slave processor comprises means for comparing the maximum amplitude and width of an ventricle pacing stimulation pulse signal received from the pacing stimulation signal source with the strength duration table stored in the memory associated therewith to determine whether the received ventricle pacing stimulation signal exceeds both amplitude and width characteristics represented by data of any table entry;

wherein said signal means comprises means for providing an atrial pacing signal to the heart model in response to a received atrial pacing stimulation signal that exceeds said amplitude and width characteristics represented by a table entry in the memory associated with the atrial slave processor; and wherein said signal means comprises means for providing a ventricle pacing signal to the heart model in response to a received ventricle pacing stimulation signal that exceeds said amplitude and width characteristics represented by a table entry in the memory associated with the ventricle slave processor.

* * * * *